United States Patent [19]

Yamamoto et al.

[11] Patent Number: 5,498,527
[45] Date of Patent: Mar. 12, 1996

[54] PHOSPHORYLCHOLINE-CONTAINING GLYCEROGLYCOLIPID

[75] Inventors: Naoki Yamamoto; Kazuhiro Matsuda, both of Tokyo, Japan

[73] Assignee: Ube Industries, Ltd., Yamaguchi, Japan

[21] Appl. No.: 251,479

[22] Filed: May 31, 1994

[30] Foreign Application Priority Data

Feb. 18, 1994 [JP] Japan ................... 6-021429

[51] Int. Cl.⁶ ............... C12Q 1/04; C12Q 1/00; C12P 9/00; C12P 7/64
[52] U.S. Cl. ............. 435/34; 435/4; 435/131; 435/132; 435/134; 536/26.1; 536/55.1; 536/117; 536/123.1; 424/264.1
[58] Field of Search ............... 435/34, 26, 131, 435/199, 195, 25, 4, 132, 134; 536/55.1, 26.1, 117, 123.1; 424/264.1

[56] References Cited

U.S. PATENT DOCUMENTS

| | | | |
|---|---|---|---|
| 4,612,281 | 9/1986 | Desmonts et al. | 435/34 |
| 4,782,019 | 11/1988 | Kokusho et al. | 435/131 |
| 4,965,353 | 10/1990 | della Valle et al. | 536/55.1 |
| 4,985,243 | 1/1991 | Faulds et al. | 435/199 |
| 5,035,995 | 7/1991 | Taguchi et al. | 435/26 |
| 5,091,307 | 2/1992 | Escarguel et al. | 435/34 |
| 5,093,238 | 3/1992 | Yamashoji et al. | 435/34 |
| 5,278,064 | 1/1994 | Berry et al. | 435/195 |

OTHER PUBLICATIONS

Nishida et al, Tetrahedron Letters, vol. 35, No. 30, pp. 5465–5468, 1994.
Maniloff et al, "Mycoplasmas" Molecular Biology & Pathogenesis, pp. 435–436, 1992.
Hayflick, Leonard; "Biology of the Mycoplasma", pp. 680–681, 1967.

*Primary Examiner*—Michael G. Wityshyn
*Assistant Examiner*—Louise N. Leary
*Attorney, Agent, or Firm*—McAulay Fisher Nissen Goldberg & Kiel

[57] ABSTRACT

The invention is directed to the compound 1'-[2,3-Bis(hexadecanoyloxy)propyl] -d-glycopyranos-6'-yl-2"-(trimethylammonium)ethylphosphate which is a phosphorylcholine-containing glyceroglycolipid useful for detecting the presence of *Mycoplasma fermentans* in cells or microorganisms.

1 Claim, 4 Drawing Sheets

$(M+H)^+$, 896

$(M+H)^+, 896$

Proton NMR

PHOSPHORYLCHOLINE-CONTAINING GLYCEROGLYCOLIPID

BACKGROUND OF THE INVENTION

1. Field of Invention

This invention relates to a new phosphorylcholine-containing glyceroglycolipid which is recovered from a lipid fraction of *Mycoplasma fermentans* GGPL (glyceroglycophosphorylcholine) strain.

2. Description of Prior Art

It is known that HTLV-I (Human T cell leukemia virus-I) and HIV (Human Immunodeficiency virus), both of which belong to human retrovirus, easily infect Helper T cell among lymphocyte. HTLV-I monoclonally changes the infected cell into tumor, while HIV breaks the infected cell to cause AIDS (Acquired Immune Deficiency Syndrome). It is reported that *Mycoplasma fermentans* takes a part in the process to cause AIDS by HIV in the infected cell. Also reported is that *Mycoplasma fermentans* is closely related to conditions of rheumatism. However, no detailed studies have been reported.

SUMMARY OF THE INVENTION

As a result of study by the inventors on human T cell which is superinfected with *Mycoplasma fermentans* and HTLV-1, it has been discovered that a new phosphorylcholine-containing glyceroglycolipid is present in a lipid fraction extracted from the infected cell.

The present invention provides 1'-[2,3-bis(hexadecanoyloxy)propyl] -d-glycopyranos-6'-yl-2"-(trimethylammonium) ethylphosphate, which is a new phosphorylcholine-containing glyceroglycolipid recovered from a lipid fraction of *Mycoplasma fermentans* GGPL strain.

1'-[2,3-Bis(hexadecanoyloxy)propyl]-d-glycopyranos-6'-yl- 2"-(trimethylammonium) ethylphosphate of the invention has the following formula:

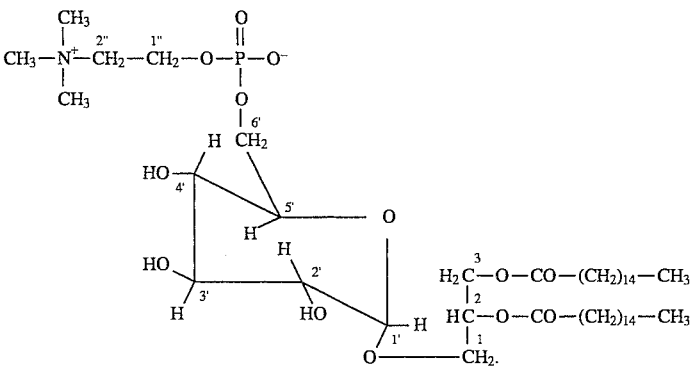

The above compound can be named 1,2-di-O-palmitoyl-3-O-[ 6-O-(2-trimethylaminoethoxy)-phosphinate-α-D-glucopyranosyl] -sn-glycerol of the following formula, from the viewpoint that the compound is a glycerol derivative:

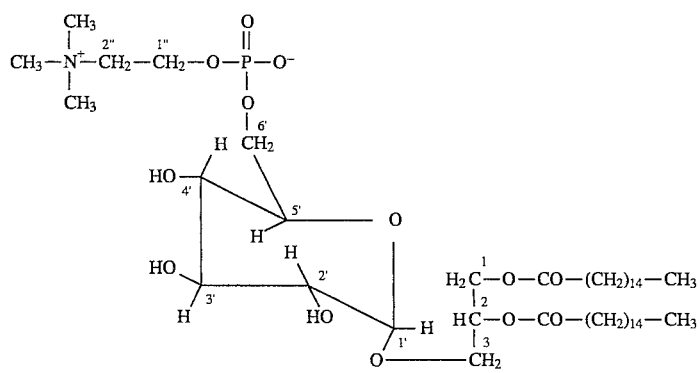

The invention further resides in a method for detecting *Mycoplasma fermentans* by detecting 1'-[2,3-Bis(hexadecanoyloxy)propyl] -d-glycopyranos-6'-yl-2"-(trimethylammonium) ethylphosphate in cells or microorganisms.

DETAILED DESCRIPTION OF THE INVENTION

Figure 1:
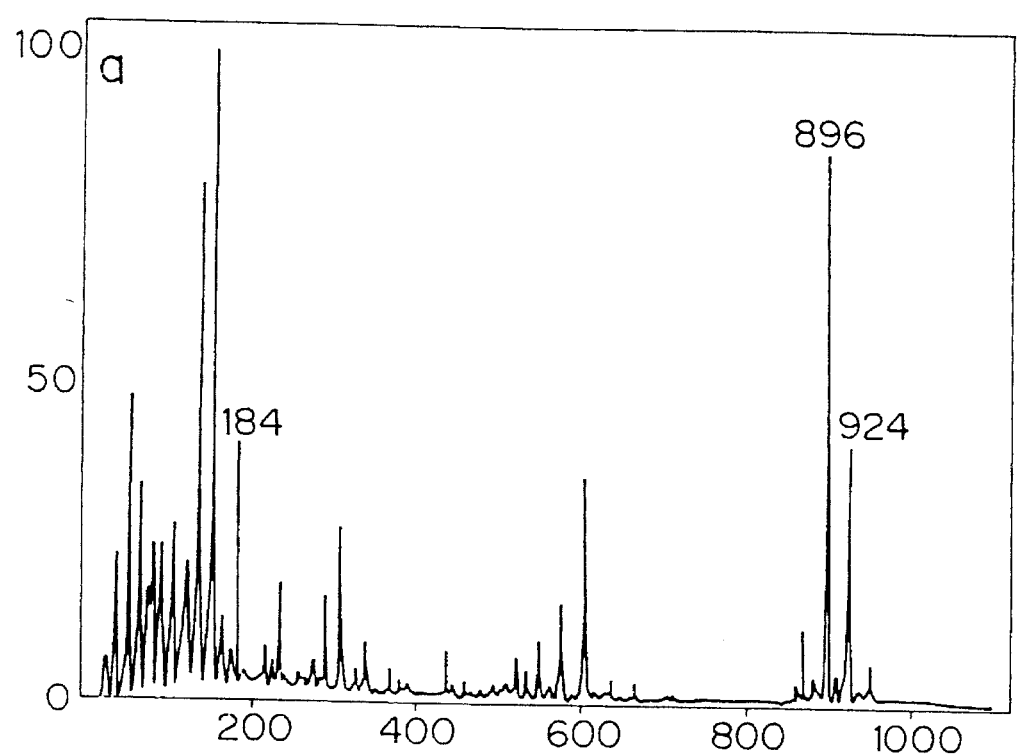
FIG. 1 is a chart which shows results of the positive-LSIMS of GGPL-I corresponding to the glycolipid of the invention.

The new phosphorylcholine-containing glyceroglycolipid of the invention having the above formula is contained in *Mycoplasma fermentans*. Accordingly, this new glyceroglycolipid can be employed for determining the presence of *Mycoplasma fermentans* in cells.

The present invention is further described by the following Examples.

EXAMPLE 1

(1) Procedures

1) Fermentation

*Mycoplasma fermentans* GGPL strain was cultured on a PPLO medium to grow cells of Micoplasma. The cells were twice washed with PBS (phosphate-buffered saline) and kept at −80° C.

2) Extract of lipid

A lipid was extracted from the cells three times using 400 ml of a mixture of chloroform and methanol (three portions, 2:1, 1:1, and 1:2). Thus, 993 mg of a total lipid was obtained.

3) Fraction A (non-bonding fraction)

The total lipid was subjected to column chromatography using DEAE (Sephadex A-25 column) to give a non-bonding fraction and a bonding fraction. There was obtained 775 mg of the non-bonding fraction.

4) Fraction B (phosphorylcholine-containing glyceroglycolipid)

The non-bonding fraction (fraction A) was subjected to chromatography using Iatrobeads and three portions of mixtures of chloroform, methanol, and water at varying ratios (from 83:16:0.5 to 20:80:8) to collect fractions containing a phosphorylcholine-containing glyceroglycolipid as well as lysophosphatidylcholine (lysoPC). The determination of the presence of phosphorylcholine-containing glyceroglycolipid in the fractions was performed using an oricinol-$H_2SO_4$ reagent (detection of saccharide) and Dittmer reagent (detection of phosphorous).

The fractions were then combined and subjected to chromatography using Iatrobeads and eluting by the gradient method which used mixtures of 1-propanol, ammonia, and water at varying ratios (from 80:5:15 to 75:5:20, volume ratio) to obtain fractions which contained GGPL-I but did not contain lysoPC. The yield of GGPL-I was 3 mg (by TLC). In this gradient method, decomposition of the obtained ester (GGPL-I) was prevented by neutralizing immediately the eluted fractions with acetic acid.

5) Analysis by mass spectroscopy

GGPL-I was subjected to mass spectroscopic analysis using mass spectrometer (available from Finnegan-Mat, TSQ- 70 triplet-stage quadropole mass spectrometer) to perform LSIMS (liquid secondary ion mass spectrometry) and MS/MS analysis.

6) Analysis by NMR spectroscopy

GGPL-I was dissolved in 0.5 ml of $(CH_3)_2SO-D_6/D_2O$ (98:2) and subjected to $^1$H- and $^{13}$C-NMR spectroscopy at 60° C. using NMR spectrometer (available from Japan Electron Co., Ltd.: FX-400).

(2) Results of analysis a) Characteristics

GGPL-I is positive to oricinol-$H_2SO_4$ reagent, Dittmer reagent, and Dragendorff reagent (detection of choline), and is decomposed in a weak alkaline solution.

b) FTIR analysis

IR analysis teaches that GGPL-I has an absorption at 960 cm$^{-1}$ (assigned to choline moiety) as well as absorptions at 1740 cm$^{-1}$ and 1170 cm$^{-1}$ (assigned to ester bonding).

c) LSIMS (Liquid secondary ion mass spectrometry) and MS/MS analysis

The spectrum of the positive ion-LSIMS of GGPL-I is shown in FIG. 1. There is observed signals at m/z 896 and 924 corresponding to molecular ion.

Figure 2:
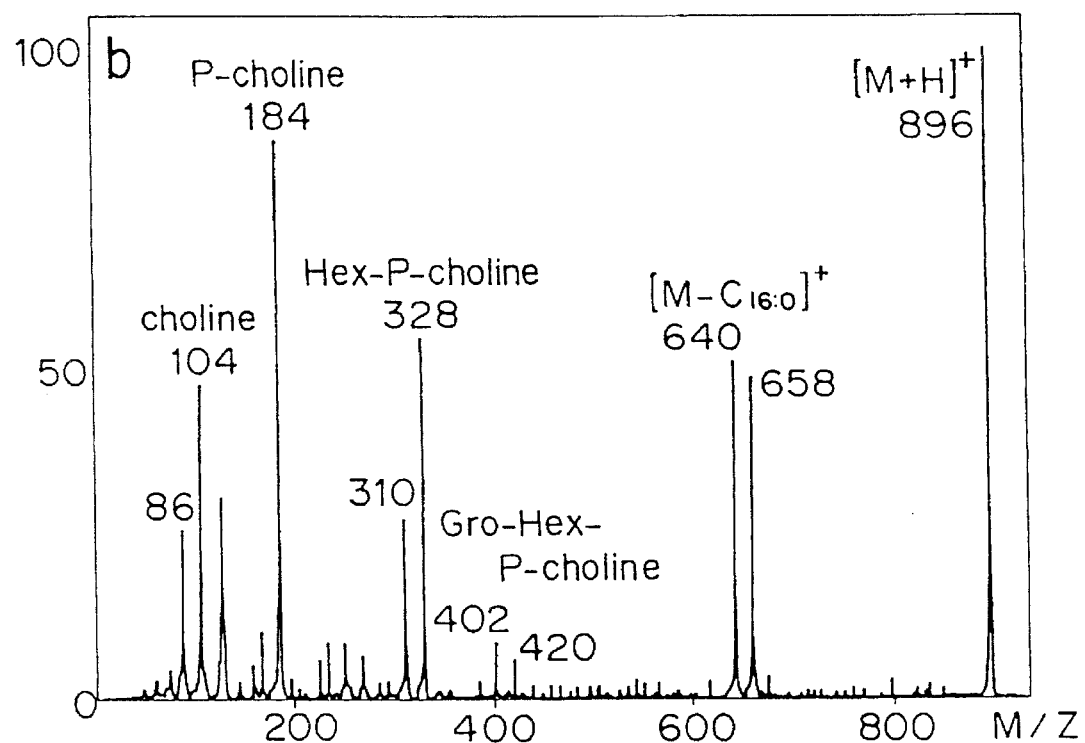
FIG. 2 is a chart which shows results of the MS/MS analysis of GGPL-I.

MS/MS analysis of the molecular ion corresponding to m/z 896 gives the spectrum shown in FIG. 2, in which assignment of most of the principal signals are indicated.

In FIG. 2, the signals correspond the following moieties: M—$C_{16:0}$ (palmitic acid), Gro-Hex-P-choline (glycerol hexose phosphorylcholine), Hex-P-choline (hexose phosphorylcholine), and P-choline (phosphorylcholine).

Accordingly, it is assumed that [M+H]$^+$896 corresponds to a glyceroglycolipid in which two $C_{16:0}$ fatty acid moieties are attached to a glycerol-hexose-phosphorylcoline.

d) NMR analysis ($^1$H-NMR)

Figure 3:
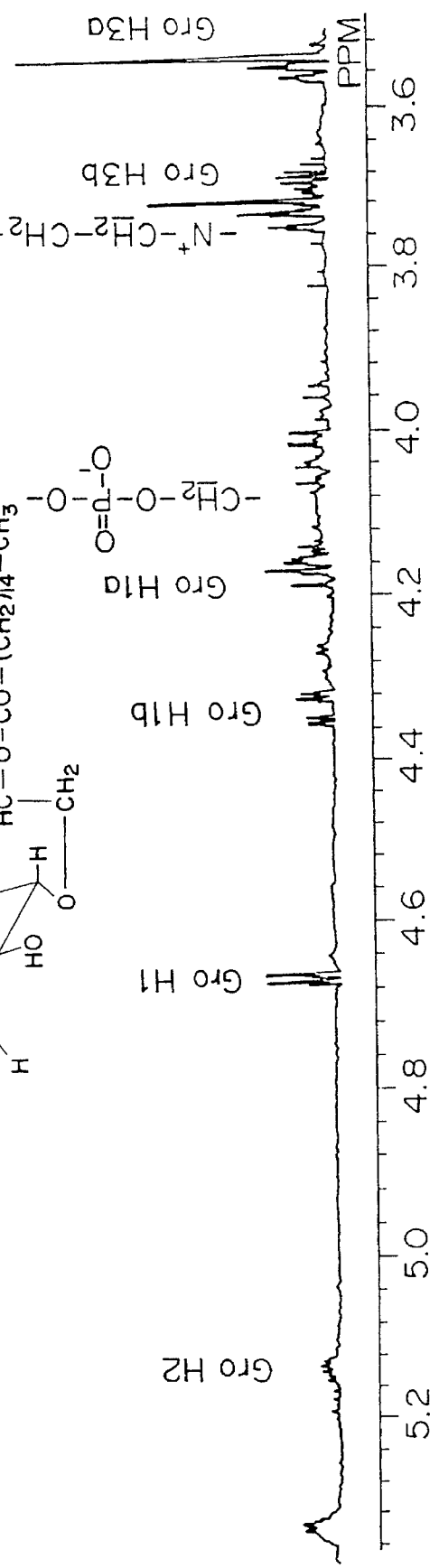
FIG. 3 is a chart which shows results of $^1$H-NMR of GGPL-I.

NMR spectrum ($^1$H-NMR) of GGPL-I is shown in FIG. 3. In the spectrum, the crosspeak of protons at the 1- and 3-positions resonated with the proton peak indicates the presence of a diacylglycerol moiety (hereinafter referred to as Gro). Also indicated is that the nucleus is α-glucose to which a phosphorylcholine moiety is attached to the 6-position of α-glucose and the glycerol moiety is attached to the 1-position of α-glucose.

It is further confirmed that the chemical shifts and coupling constants of the phosphoric acid site, N-site, and carbon atom of methyl group in the choline structure agree with those of a reference sample of PC.

Based on the above observation, it is concluded that GGPL-I contains 1 mole of a glycerol moiety, 2 moles of fatty acid moieties, 1 mole of an α-glucose moiety (saccharide moiety), and 1 mole of a phosphorylcholine moiety, and that the phosphorylcholine moiety is attached to the α-glucose moiety at the 6'-position.

e) Conclusion

The analytical results indicate that the GGPL-I is 1'-[ 2,3-bis(hexadecanoyloxy)propyl]-d-glycopyranos-6'-yl-2"-(trimethylammonium) ethylphosphate having the aforementioned formula. A glycolipid having such structure is not known and accordingly is new. It is interesting that the compound of this type having a phosphorylcholine moiety is not known, while a number of glyceroglycolipids have been isolated from plant or bacteria. Further, it is noted that no glycolipid having an α-glucose moiety and a phosphorylcholine attached thereto. Glycolipids have been also isolated from brain and spermary of mammals. However, these glycolipids contain no α-glucose moiety to which phosphorylcholine moiety is attached.

EXAMPLE 2

1'-[2,3-Bis(hexadecanoyloxy)propyl]-d-glycopyranos-6'-yl- 2"-(trimethylammonium) ethylphosphate of the invention {which is also called 1,2-di-O-palmitoyl-3-O-[6-O-(2-trimethylaminoethoxy)-phosphinate-α -D-glucopyranosyl]-sn-glycerol} which is discovered in *Mycoplasma fermentans* GGPL strain can be synthesized by the following process from the known compound.

In the process, the post treatment means a procedure which comprises dilution with methylene chloride, washing with water, washing with a saturated aqueous sodium hydrogen carbonate solution, drying over anhydrous magnesium sulfate, filtering over Celite, and concentration under reduced pressure to distill off volatile materials, as performed in series.

(1) Synthesis of 2,3,4-tri-O-benzyl-6-O-p-nitrobenzoyl-α -D-glucopyranosyl bromide In 15 ml of methylene chloride saturated with hydrogen bromide is stirred at room temperature for 30 min. 1.45 g (1.94 mmol) of 2,3,4-tri-O-benzyl-1,6-di-O-p-nitrobenzoyl-D-glucopyranose. The reaction mixture is filtered over Celite, and the filtrate is concentrated under reduced pressure. The residue is dissolved in 5 ml of methylene chloride, and the solution is again placed under reduced pressure. There is obtained 2,3,4-tri-O-benzyl-6-O-p-nitrobenzoyl-α -D-glucopyranosyl bromide as a syrup.

(2) Synthesis of 1,2-anhydro-3-O-[2,3,4-tri-O-benzyl-6-O-p-nitrobenzoyl-α-D-glucopyranosyl]-sn-glycerol In 10 ml of methylene chloride is stirred at room temperature for 15 min. a mixture of 720 mg (9.7 mmol) of (S)-glycidol (glycide), 338 mg (2.9 mmol) of tetramethylurea, 440 mg (3.8 mmol) of tetraethylammonium bromide, and 300 mg of powdery molecular sieve 3A. To the obtained methylene chloride solution is added at room temperature for 5 min. 1.45 g of 2,3,4-tri-O-benzyl-1,6-O-p-nitrobenzoyl-α -D-glucopyranosyl bromide in 5 ml of methylene chloride. The resulting mixture is stirred overnight. The mixture is then subjected to the post treatment. The obtained syrup is purified by silica gel column chromatography (eluent: toluene:ethyl acetate=10:1) to give 972 mg of the captioned compound as a syrup. Yield 78%.

(3) Synthesis of 1,2-anhydro-3-O-[2,3,4-tri-O-benzyl-α -D-glucopyranosyl]-sn-glycerol The syrup (500 mg) of 1,2-anhydro-3-O-[2,3,4-tri-O-benzyl- 6-O-p-nitrobenzoyl-α-D-glucopyranosyl]-sn-glycerol is stirred in 10 ml of a methanol solution containing 10 mg of sodium methoxide for 3 hours. The mixture is then neutralized with Amberlyst 15 (H$^+$ type) to give 384 mg of the captioned compound as a syrup. Yield: 100%. $[\alpha]^{22}_D$:+ 38° (CHCl$_3$, c 0.1)

(4) Synthesis of 1-O-palmitoyl-3-O-[2,3,4-tri-O-benzyl-α -D-glucopyranosyl]-sn-glycerol In 10 ml of dimethylformamide containing 300 mg (0.61 mmol) of 1,2-anhydro-3-O-[2,3,4-tri-O-benzyl-α-D-glucopyranosyl] -sn-glycerol are placed 1 g of palmitic acid and 650 mg of cesium carbonate. The mixture is then stirred at 120°–130° C. for 8 hours. The reaction mixture is filtered and subjected to the post treatment to give 390 mg of the captioned compound as a wax. Yield: 85%. $[\alpha]^{22}_D$:+25° (CHCl$_3$, c 0.2)

(5) Synthesis of 1,2-di-O-palmitoyl-3-O-[2,3,4-tri-O-benzyl- 6-O-tert-butyldimethylsilyl-α-D-glucopyranosyl]-sn-glycerol To a mixture of 200 mg (0.26 mmol) of 1-O-palmitoyl-3-O-[ 2,3,4-tri-O-benzyl-α-D-glucopyranosyl]-sn-glycerol, 0.2 ml of triethylamine, 100 mg of N,N-dimethylaminopyridine in 10 ml of methylene chloride is added under stirring 0.5 ml of methylene chloride solution containing 50 mg (0.33 mmol) of tert-butyldimethylsilyl chloride. The mixture is stirred at room temperature for 12 hours, and to the mixture is added 150 mg (0.55 mmol) of palmitoyl chloride. The resulting mixture is stirred for 6 hours, and after addition of 0.2 ml of water, the mixture is further stirred for 30 min. The organic portion is taken out and subjected to the post treatment. Thus treated product is purified by silica gel column chromatography (eluent: n-hexane:ethyl acetate= 50:1) to give 252 mg of the captioned compound as a syrup. Yield: 86%.

(6) Synthesis of 1,2-di-O-palmitoyl-3-O-[2,3,4-tri-O-benzyl-α -D-glucopyranosyl]-sn-glycerol In 0.9 ml of methanol are stirred at room temperature for 12 hours 200 mg (0.18 mmol) of 1,2-di-O-palmitoyl-3-O-[ 2,3,4-tri-O-benzyl-6-O-tert-butyldimethylsilyl-α-D-glucopyranosyl] -sn-glycerol and 0.1 ml of trifluoroacetic acid. The reaction mixture is concentrated under reduced pressure, and after addition of toluene, is repeatedly concentrated under reduced pressure. The residue is purified by silica gel column chromatography (eluent: toluene:ethyl acetate=5:1) to give 170 mg of the captioned compound as a wax. Yield: 95%. $[\alpha]^{22}_D$:+23° (CHCl$_3$, c 0.2)

(7) Synthesis of 1,2-di-O-palmitoyl-3-O-[2,3,4-tri-O-benzyl- 6-O-(2-bromoethoxy)-phosphinate-α-D-glucopyranosyl] -sn-glycerol To 150 mg (0.15 mmol) of 1,2-di-O-palmitoyl-3-O-[ 2,3,4-tri-O-benzyl-α-D-glucopyranosyl]-sn-glycerol in 3.2 ml of trichloroethylene is added 2 ml of a trichloroethylene solution containing 0.12 ml of triethylamine and 100 mg of 2-bromoethylphosphoryl dichloride. The mixture is then stirred at room temperature for 12 hours. To the reaction mixture are added 5 ml of ethyl ether and 0.1 ml of triethylamine, and the obtained mixture is refluxed for 2 hours. The refluxed mixture is cooled, and made acidic by addition of 5% hydrochloric acid. The acidic mixture is extracted with ethyl ether. The ether portion is washed with a saturated aqueous sodium chloride solution and dried over anhydrous magnesium sulfate. The dried solution is concentrated and purified by silica gel column chromatography (eluent: chloroform:methanol=10:1) to give 141 mg of the captioned compound as a syrup. Yield: 79%. $[\alpha]^{22}_D$:+11.4° (CHCl$_3$, c 0.35)

(8) Synthesis of 1,2-di-O-palmitoyl-3-O-[2,3,4-tri-O-benzyl- 6-O-(2-trimethylaminoethoxy)-phosphinate-α-D-glucopyranosyl] -sn-glycerol In 3 ml of a mixture of chloroform/2-propanol/dimethylformamide (3/5/5) saturated with gaseous triethylamine is dissolved 100 mg (0.08 mmol) of 1,2-di-O-palmitoyl- 3-O-[2,3,4-tri-O-benzyl-6-O-(2-bromoethoxy)phosphinate-α -D-glucopyranosyl]-sn-glycerol. The solution is heated to 70° C. for 8 hours, and cooled. To the cooled mixture is added silver carbonate. The reaction mixture is refluxed at 70° C. for one hour, and then cooled to room temperature. The mixture is filtered over Celite, and the filtrate is concentrated. The residue is purified by silica gel column chromatography (eluent: chloroform:methanol= 1:1) to give 61 mg of the captioned compound as a syrup. Yield: 62%. $[\alpha]^{22}_D$:+30.0° (CHCl$_3$, c 0.04)

(9) Synthesis of 1,2-di-O-palmitoyl-3-O-[6-O-(2-trimethylaminoethoxy)-phosphinate-α -D-glucopyranosyl]-sn-glycerol A mixture of 50 mg (0.04 mmol) of 1,2-di-O-palmitoyl-3-O-[2,3,4-tri-O-benzyl-6-O-(2-trimethylaminoethoxy-)phosphinate-α -D-glucopyranosyl]-sn-glycerol and 50 mg of palladium hydroxide [Pd(OH)$_2$] in 5 ml of a mixture of methanol, water and acetic acid (10:1:1) is treated with hydrogen gas at room temperature for 12 hours. The reaction mixture is filtered and placed under reduced pressure to give 35 mg of the captioned compound, that is, 1,2-di-O-palmitoyl- 3-O-[6-O-(2-trimethylaminoethoxy)-phosphinate-α-D-glucopyranosyl] -sn-glycerol as a wax. Yield: 91%. $[\alpha]^{22}_D$:+24.9° (CHCl$_3$:methanol=2:1, c 0.06)

FB-MS: 897 (M+1)

$^1$H-NMR ( DMSO-d$_6$):

3.13 (9H, s, N(CH$_3$)$_3$), 3.53 (1H, dd, J=5.4, 11.0 Hz, H-3a), 3.68 (1H, dd, J=5.2, 11.0 Hz, H-3b), 4.32 (1H, dd, J=3.2, 11.8 Hz, H-1a), 4.14 (1H, dd, J=6.7, 11.8 Hz, H-1b), 4.65 (1H, d, J=3.6 Hz, H-1')

EXAMPLE 3

1) Fermentation

Each of seven different strains of Mycoplasma is separately cultured at 37° C. in 100 ml of a liquid medium which is prepared by adding 10% (v/v) of bovine serum, penicillin, 0.0002% (w/v) of phenol red, and 1% glucose to the PPLO liquid basic medium (available from Difco). After checking growth of Mycoplasma by change of pH in the medium, the medium is subjected to centrifugal separation at 16,000G for one hour to collect the microorganism. The microorganism is washed by dispersing it in 10 ml of a phosphate buffered saline (PBS: pH 7.4) and subjecting the dispersion to centrifugal separation at 16,000 G for one hour. The same washing procedure is repeated once. Thus obtained microorganism is a sample for extraction of a lipid.

MT-4 (GGPL+) cell which is infected with *Mycoplasma fermentans* GGPL is also processed to prepare a sample for extraction of a lipid.

2) Extraction of lipid

The microorganism sample is suspended in 10 ml of methanol, and kept for 4 hours. To the suspension is added 20 ml of chloroform to give a mixture solvent of chloroform/methanol of 2/1. The microorganism is broken using ultrasonic and kept for 4 hours. The suspension is then subjected to centrifugal separation at 3,000 rpm. The supernatant is collected and evaporated to obtain the desired lipid.

3) Fractionation

The fractionation is performed using a developing solvent of chloroform, methanol, and 0.2% aqueous calcium chloride solution (55:45:10). Thus obtained fractions are examined by Ditter reagent (for detection of phospholipid) and further by the oricinol-H$_2$SO$_4$ reagent (for detection of glycolipid) through the dyeing process.

4) TLC analysis

The lipid-containing fractions obtained from the eight samples are developed on TLC and dyed to visualize the developed bands.

Figure 4:
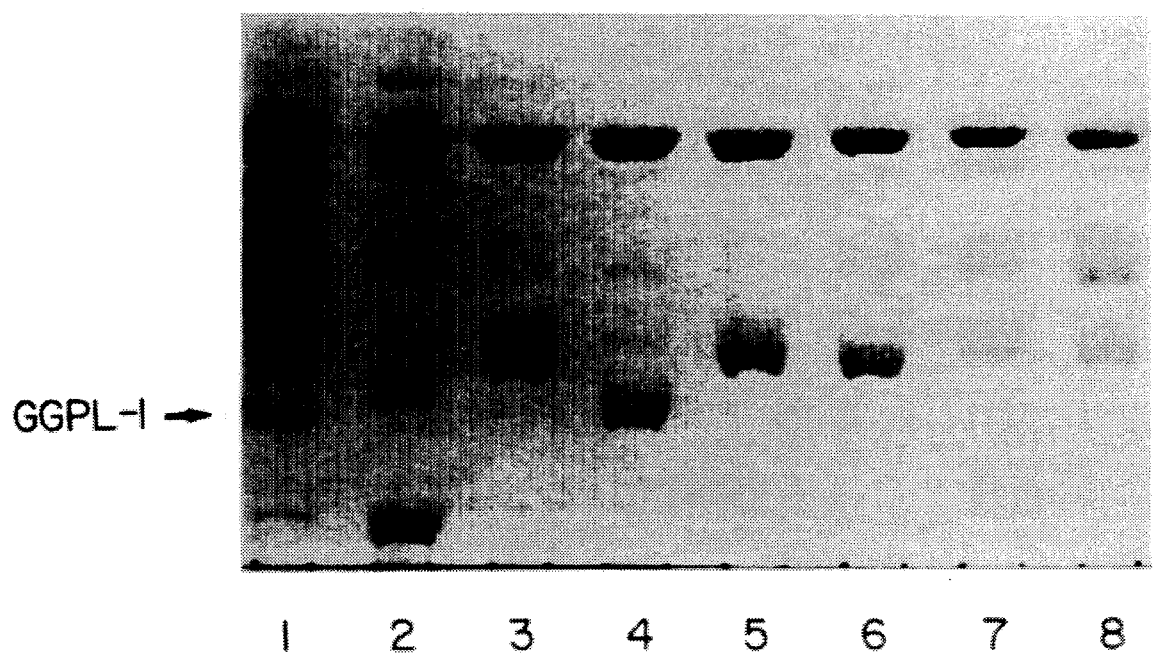
FIG. 4 shows results of TLC analysis on lipid-containing fractions obtained various Mycoplasma strains and MT-4 (GGPL+) cell which is infected with *Mycoplasma fermentans*.

The bands observed TLC are given in FIG. 4. The numbers of the lanes correspond the lipid-containing fractions from the following samples:

No. 1: MT-4 (GGPL+) cell
No. 2: *Mycoplasma fermentans* GGPL strain
No. 3: *Mycoplasma arginini* G230 strain
No. 4: *Mycoplasma fermentans* PG18 strain
No. 5: *Mycoplasma hyorhinis* DBS1050 strain
No. 6: *Mycoplasma orale* CH19199 strain
No. 7: *Mycoplasma penetrans* GTU-54-6A1 strain
No. 8: *Mycoplasma salivarium* PG20 strain According to FIG. 4, the bands indicating GGPL-I are observed only in Lane No. 1 (lane of T cell infected with *Mycoplasma fermentans*, Lane No. 2 (lane of *Mycoplasma fermentans* GGPL strain), and Lane 4 (lane of *Mycoplasma fermentans* PG18 strain. No corresponding bands are observed in other lanes.

5) Immune reaction

Immune reaction is examined using a polyclonal antibody which is prepared by immunizing a rabbit with *Mycoplasma fermentans*. It is confirmed that the band corresponding to GGPL-I only is immunologically responsive to the polyclonal antibody.

It is further confirmed that the bands of lanes of *Mycoplasma fermentans* are not responsive to antisera prepared by immunizing rabbits with various Mycoplasma species other than *Mycoplasma fermentans*.

We claim:

1. 1'-[2,3-Bis(hexadecanoyloxy)propyl]-d-glycopyranos-6'-yl-2''-(trimethylammonium) ethylphosphate.

* * * * *